(12) United States Patent
Tabatabaei et al.

(10) Patent No.: US 6,206,900 B1
(45) Date of Patent: Mar. 27, 2001

(54) CLOT EVACUATION CATHETER

(75) Inventors: Shahin Tabatabaei, Malden; W. Scott McDougal, Manchester, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/330,699

(22) Filed: Jun. 11, 1999

(51) Int. Cl.$^7$ ........................................ A61B 17/32
(52) U.S. Cl. ................................ 606/170; 606/180
(58) Field of Search ..................... 606/170, 180; 600/562, 564, 565, 567, 568

(56) References Cited

U.S. PATENT DOCUMENTS

| | | |
|---|---|---|
| 4,020,847 | 5/1977 | Clark, III . |
| 4,167,943 * | 9/1979 | Banko . |
| 4,631,052 * | 12/1986 | Kensey . |
| 4,754,755 | 7/1988 | Husted . |
| 4,790,812 | 12/1988 | Hawkins, Jr. et al. ................ 604/22 |
| 4,815,462 * | 3/1989 | Clark . |
| 5,507,760 | 4/1996 | Wynne et al. ........................ 606/159 |
| 5,520,635 | 5/1996 | Gelbfish ................................ 604/22 |
| 5,569,275 * | 10/1996 | Kotula et al. .................... 606/170 X |
| 5,643,296 | 7/1997 | Hundertmark et al. ............. 606/159 |
| 5,807,401 * | 9/1998 | Grieshaber et al. ................. 606/107 |

FOREIGN PATENT DOCUMENTS

4038398 * 6/1992 (DE) .................................... 606/180

* cited by examiner

Primary Examiner—Jeffrey A. Smith
(74) Attorney, Agent, or Firm—Nutter, McClennen & Fish, LLP; William C. Geary, III; Richard J. Roos

(57) ABSTRACT

A clot evacuation catheter includes a hollow tubular body disposed within an outer lumen. The tubular body is elongate and includes a selectively rotatable cutting blade disposed within a distal portion thereof to cut clots occluded in at least one opening of the cutting blade. The tubular body also includes a fluid conveying irrigation lumen to deliver fluid to a distal end of the catheter at predetermined times. In an alternative embodiment of the present invention, a hood member extends from the distal portion of the tubular body. The hood member has a distal end that is spaced from, but coaxial with, the distal portion of the tubular body through a side portion of the hood member.

21 Claims, 3 Drawing Sheets

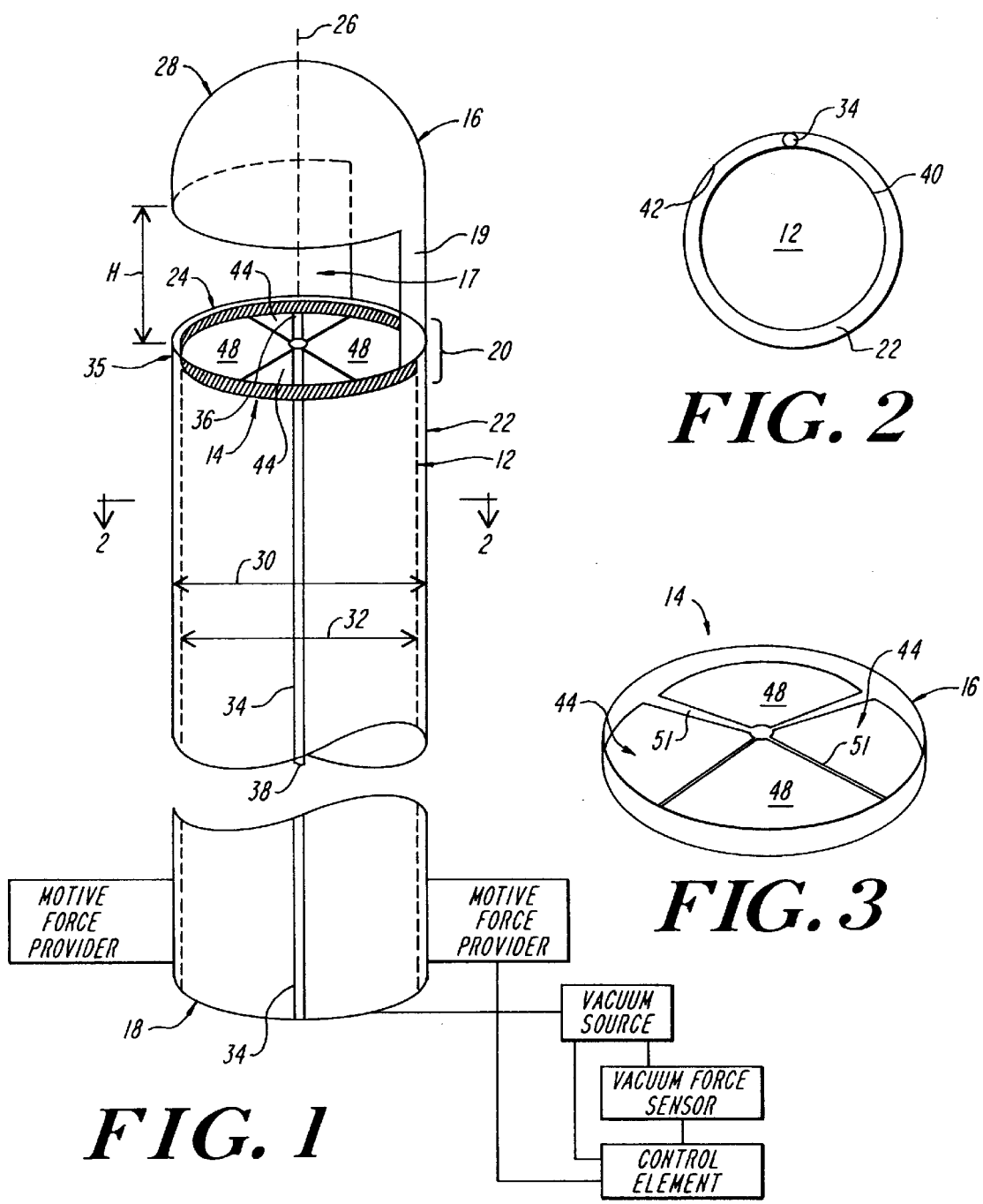

CLOT EVACUATION CATHETER

CROSS-REFERENCE TO RELATED APPLICATIONS

Not applicable.

STATEMENT REGARDING FEDERALLY-SPONSORED RESEARCH

Not applicable.

FIELD OF THE INVENTION

The invention relates to clot removal devices. More particularly, the invention relates to catheters for evacuating clots from the bladder or thick fluids from hollow viscera or cavities.

BACKGROUND OF THE INVENTION

Urological procedures, such as operations and/or pathology on the bladder and prostate, are commonly performed. A complication that may arise as a result of such urological procedures being performed, or as a result of diseases of the bladder or prostate, is the accumulation and retention of clots in the bladder or prostate.

The presence of these clots, and the danger they potentially pose to a patient, have been known for decades. Many techniques and associated devices have been employed in order to eliminate these bladder clots. Most techniques involve the insertion of catheters to irrigate and then evacuate the clots. For example, one specific technique involves the insertion of a 3-way Foley catheter to irrigate the bladder followed by the replacement of the Foley catheter with a Whistle tip catheter to further irrigate the bladder and suction away clots.

While this clot evacuation technique usually works for its intended purpose, it is replete with disadvantages and associated problems involving patient discomfort, duration, cost and risk. For example, the insertion and removal of a catheter on two separate occasions during one procedure increases the likelihood of triggering acute senses of invasiveness and discomfort in a patient. Also, when especially large clots are present and need to be evacuated, correspondingly large catheters must be used, thus necessitating the use of general anesthesia.

Another problem with this, and other techniques that employ more than one catheter, is that certain remote but realistic risks to a patient arise upon each insertion of a catheter (i.e., bladder injury or rupture, bacteremia) and accompany any usage of general anesthesia (i.e., allergic reaction by the patient, overdose). Furthermore, these prior art clot evacuation techniques are costly due to the surgical time required and the use of general anesthesia.

Another technique for eliminating clots in the bladder or prostate is to cut the clots with a catheter equipped with cutting blades. Catheters equipped with cutting blades, however, have yet to adequately reconcile safety issues with performance issues. For example, large and powerful blades are required to cut large bladder clots; however, such catheters do not adequately protect the bladder wall from being cut while the blade is active.

Various clot evacuation catheters are shown and described in U.S. Pat. Nos. 4,020,847 (to Clark, III); 4,631,052 (to Kensey); 4,754,755 (to Husted); 4,790,812 (to Hawkins, Jr. et al.); 5,520,635 (to Gelbfish) and 5,643,296 (to Hundertmark).

A need remains, however, for a catheter which will enable the effective removal of clots of varying size from the bladder and/or prostate while minimizing the cost and duration of the process, and the discomfort and risk of harm to the patient during the process.

SUMMARY OF THE INVENTION

The present invention provides a clot evacuation catheter. Although the invention is primarily shown and described as a device to cut and evacuate clots from the bladder, it is understood that the device has other applications as well.

The clot evacuation catheter includes a tubular body disposed within an outer lumen. The outer lumen and tubular body are concentric and have coaxial longitudinal axes. The outer lumen has an open distal end, and the tubular body has a distal portion with an opening therein.

The tubular body is elongate and hollow and has a cutting blade disposed within the distal portion thereof to cut clots. The cutting blade is substantially disk-shaped and is selectively rotatable in a plane transverse to the longitudinal axis of the tubular body. The cutting blade has at least one opening within which clots occlude and are cut. The cutting blade is mounted to a wall of the tubular body such that the tubular body and the cutting blade are selectively rotatable with each other. The catheter also includes a fluid conveying irrigation lumen. The irrigation lumen extends longitudinally through the catheter and has an open distal end disposed proximal to the cutting blade.

In another embodiment, the catheter further includes a hood member that is formed on and extends distally from the distal portion of the tubular body. A dome-like distal end of the hood member shrouds the distal portion of the tubular body while allowing access to the tubular body through a side opening in the hood member.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 1 is a front view, with partial cut-away, of an embodiment of the clot evacuation catheter of the present invention;

FIG. 2 is a cross-sectional view of the clot evacuation catheter of FIG. 1 taken along the line 2—2;

FIG. 3 is a perspective view of a cutting blade of the clot evacuation catheter of FIG. 1;

DETAILED DESCRIPTION OF THE INVENTION

Figure 4:
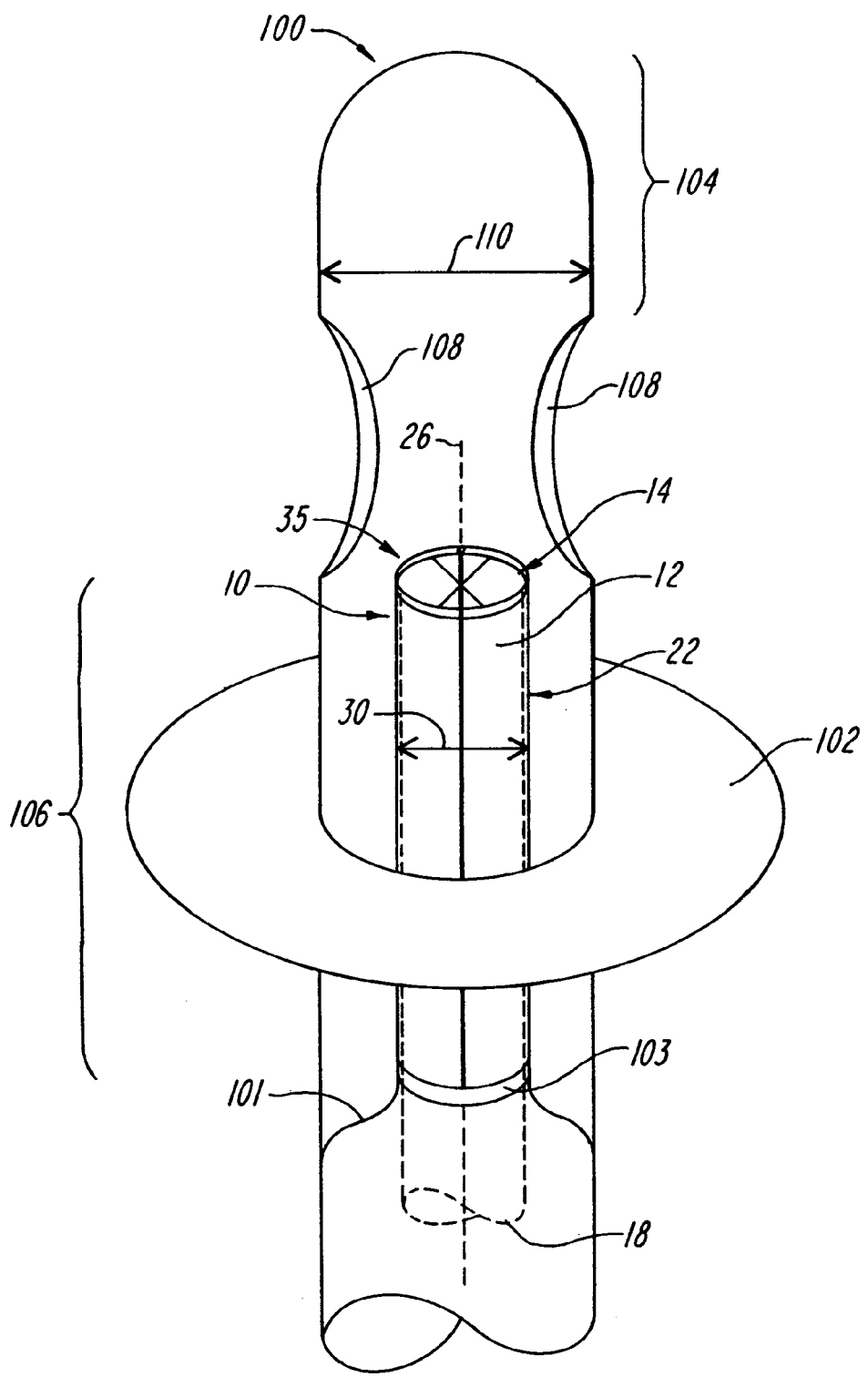
FIG. 4 is a front view, with partial cut away, of the clot evacuation catheter of FIG. 1 inserted within a Foley catheter.

A clot evacuation catheter 10 in accordance with the present invention is depicted in FIG. 1. The catheter 10 has a tubular body 12 through which clots, such as bladder clots, may be evacuated after being cut by a cutting blade 14. The tubular body 12 of the catheter 10 is elongate, hollow and substantially cylindrical, with a proximal end 18 and an open distal portion 20. The tubular body 12 is disposed within an outer lumen 22 that has an open distal end 24. The tubular body 12 and the outer lumen 22 are generally concentric, and have longitudinal axes that are coaxial with a longitudinal axis 26 of the catheter 10.

The outer lumen 22 and the tubular body 12 are each substantially cylindrical. The outer lumen 22 has a longitudinal length greater than the length of the tubular body 12 and a diameter 30 that is substantially constant and greater than the substantially constant diameter 32 of the tubular body. Whereas the tubular body 12 and the outer lumen 22 each may be adapted to rotate, the outer lumen 22 is preferably static.

The catheter 10 also includes a fluid conveying irrigation lumen 34 to deliver an irrigating fluid to a distal end 35 of the catheter 10 at predetermined times in order to soften clots. The irrigation lumen 34 is disposed within, and extends longitudinally through the tubular body 12 of the catheter 10 and is preferably static. The longitudinal length of the irrigation lumen 34 is generally less than either the length of the outer lumen 22 or the length of the tubular body 12. The irrigation lumen 34 has an open distal end 36 that is proximal to the cutting blade 14 of the catheter 10.

The irrigation lumen 34 is substantially cylindrical and has a substantially constant diameter 38. In an exemplary embodiment, the irrigation lumen 34 is contained within the outer wall 40 of the tubular body 12 and is proximal to the cutting blade 14 of catheter 10. Preferably, and as shown in FIG. 2, the irrigation lumen 34 contacts both walls 40, 42 such that the diameter 38 of the irrigation lumen is approximately equal to the difference between the diameter of the outer lumen 22 and the diameter of the tubular body 12. Alternatively, the irrigation lumen may be disposed within the tubular body 12 and/or may be positioned such that it does not contact either wall 40, 42.

The irrigation lumen 34 is adapted to provide controlled delivery of irrigating fluid to the distal end 35 of the catheter at predetermined times. In an exemplary embodiment, irrigating fluid is delivered when one or more clots occlude at least one opening 44 in the cutting blade 14. The fluid softens the clot(s) and facilitates the cutting thereof by at least one cutting member 48 of the cutting blade 14. One of ordinary skill in the art will readily appreciate that the timing of fluid delivery and the volume of fluid delivered may be varied depending upon the need of a given procedure. An exemplary irrigating fluid is saline, but one of ordinary skill in the art will also appreciate that other sterile fluids may be used as irrigation fluids.

The catheter 10 may also include a hood member 16 that extends from the distal portion 20 of the tubular body 12. In an exemplary embodiment, the hood member 16 has a closed, dome-like distal end 28 that is mounted to the tubular body 12 by a side portion 19. A side-facing space or opening 17 separates the dome-like distal end 28 of the hood member 16 from the distal portion 20 of the tubular body 12. The hood member 16 is useful to shroud the distal end 35 of the catheter, thereby preventing the cutting blade 14 from inadvertently damaging healthy tissue.

The hood member 16 preferably has a diameter greater than or approximately equal to the diameter 30 of the outer lumen 22. The side-facing opening 17 of the hood member 16 should have dimensions that are suitable to allow clots to enter the hood member and contact cutting blade 14. One of ordinary skill in the art can readily determine the dimensions of this opening. Generally, however, the opening has a height (H) of about 2.0 millimeters to 7.0 millimeters.

A cutting blade 14 useful with the present invention is shown in FIG. 1 and, in particular, FIG. 3. The cutting blade 14 should be shaped and oriented so as to be able to rotate and cut any clots that are to be evacuated. The cutting blade 14 is disposed within the distal portion 20 of the tubular body 12 of a catheter 10 and is selectively rotatable in a plane transverse to the longitudinal axis 26 of the tubular body.

In an exemplary embodiment, the cutting blade 14 is in the form of a disk-like member with an outer rim 46 and at least one opening 44 formed in the cutting blade 14. In the embodiment depicted in FIGS. 1 and 3, the cutting blade 14 has two openings 44, each of which are wedge-shaped. The location of these openings 44 results in the formation in the cutting blade 14 of two wedge-shaped cutting members 48. The edge 51 of each wedge-shaped cutting member 48 adjacent to openings 44 serves as a leading edge which, upon rotation of the cutting blade 14, is effective to cut a clot to a size small enough to enable the clot to pass through openings 44 to be evacuated through catheter 10. Although the openings 44 are described and illustrated as wedge-shaped, they may assume a variety of other shapes as well. Also, the number of openings 44 may be greater or less than two.

The dimensions of the cutting blade 14 may vary depending upon the requirements of a given application. In one embodiment, the cutting blade 14 has a diameter in the range of about 2.0 millimeters to 10.0 millimeters and a thickness of about 0.5 millimeter to 2.0 millimeters. Where two openings 44 are used, the total surface area of the cutting blade 14 occupied by the openings 44 is in the range of about 0.785 $mm^2$ to 30.00 $mm^2$, or about 50 to 75 percent of the surface area of the cutting blade. Also, the cutting blade 14 is generally disposed proximal to the distal end 24 of the tubular body 12 by a distance between about 0.1 millimeter and 1.0 millimeter.

The cutting blade 14 can be made from a variety of materials such as polymers, ceramics, metals and metal alloys. In one example, the cutting blade 14 is made from a polymer and is coated with polytetrafluoroethylene.

As noted above, the cutting blade 14 is rotated to effect cutting of clots. The catheter 10 may be designed so that the cutting blade 14 is rotatable with, or independent of the tubular body 12. In one embodiment, the cutting blade 14 may be mounted to an inner wall 40 of the tubular body 12, as shown in FIG. 1, such that the cutting blade and the tubular body are selectively rotatable with each other. The cutting blade 14 is adapted to rotate when the size or weight of clot(s) that occlude the at least one opening 44 of the cutting blade create a predetermined level of vacuum force as detected by a vacuum force sensor.

In the embodiment depicted in FIG. 1, in which the cutting blade 14 and the tubular body 12 rotate together, the proximal end 18 of the tubular body is in communication with a motive force provider that rotates the tubular body and cutting blade when a predetermined level of vacuum force (e.g., above about 30 cm $H_2O$) is detected by a vacuum force sensor. The vacuum force sensor is in communication with a control element. When a predetermined level of vacuum force is detected by the vacuum force sensor, the control element sends a signal to the motive force provider and to a vacuum source. The motive force provider then rotates the tubular body 12 and cutting blade to cut clots that occlude openings 44 in cutting blade 14. At the same time, the vacuum source applies a force in the magnitude of about 40 cm $H_2O$ to 200 cm $H_2O$ to assist in the evacuation of clots through the catheter 10.

The cutting blade 14 may alternatively be mounted within a groove, track or rail (not shown) formed within an inner wall of the tubular body 12. In such an embodiment, the groove should be of sufficient diameter and longitudinal length to allow the cutting blade to be placed, and to rotate, therein.

Referring now to FIG. 4, an alternate embodiment of the clot evacuation catheter 10 is shown disposed in a Foley catheter 100. The clot evacuation catheter 10 of FIG. 6 is substantially identical to the embodiment illustrated in FIG. 1, except that it does not include a hood member 16. The hood member 16 is generally not required in this embodiment because its function of guarding areas of the body from the cutting blade 14 is accomplished by the clot evacuation catheter 10 being disposed within the Foley catheter 100.

The Foley catheter 100 is of a type well known in the art and includes a distal portion 104, a proximal portion 106 and at least one opening 108 through which clots may pass. The Foley catheter 100 may also include an irrigation lumen (not shown), and/or other features generally known in the art to ensure, and facilitate, the entry of clots within the Foley catheter 100 and the clot evacuation catheter 10.

The catheter 10 may be disposed within the Foley catheter 100 in one of several ways generally known in the art. In the exemplary embodiment of FIG. 4, an adapter 101 is disposed around the catheter 10 and against the Foley catheter 100 with sufficient tightness to maintain the position of the catheter with respect to the Foley catheter. The position of the catheter 10 with respect to the Foley catheter 100 may be changed by loosening a nut or other tightening means 103, changing the position of the catheter, and then tightening the nut or tightening means.

In an exemplary embodiment, the Foley catheter 100 shares the longitudinal axis 26 of the catheter 10 and is surrounded by a balloon 102. The balloon 102 is effective to maintain the position of the Foley catheter 100 inside the bladder or other body area in which the Foley catheter is placed. The openings 108 of the Foley catheter 100 generally have identical dimensions and are located between the distal and proximal portions 104, 106 of the Foley catheter. The distal end 35 of the clot evacuation catheter 10 preferably is transversely aligned with the openings 108 of the Foley catheter 100 to increase the likelihood that clots which enter the Foley catheter will subsequently enter the tubular body and be cut by the cutting blade 14. The cutting blade 14 to be used with the embodiment shown in FIG. 4 may rotate with, or independent of, the tubular body 12.

The dimensions of the clot evacuation catheter 10 and its components may vary based on the dimensions of the Foley catheter 100 in which it is disposed. Generally, however, the diameter 30 of the outer lumen 22 of the clot evacuation catheter 10 will be between about 0.1 millimeter to 1.0 millimeter less than the diameter 110 of the Foley catheter 100.

Figure 5:
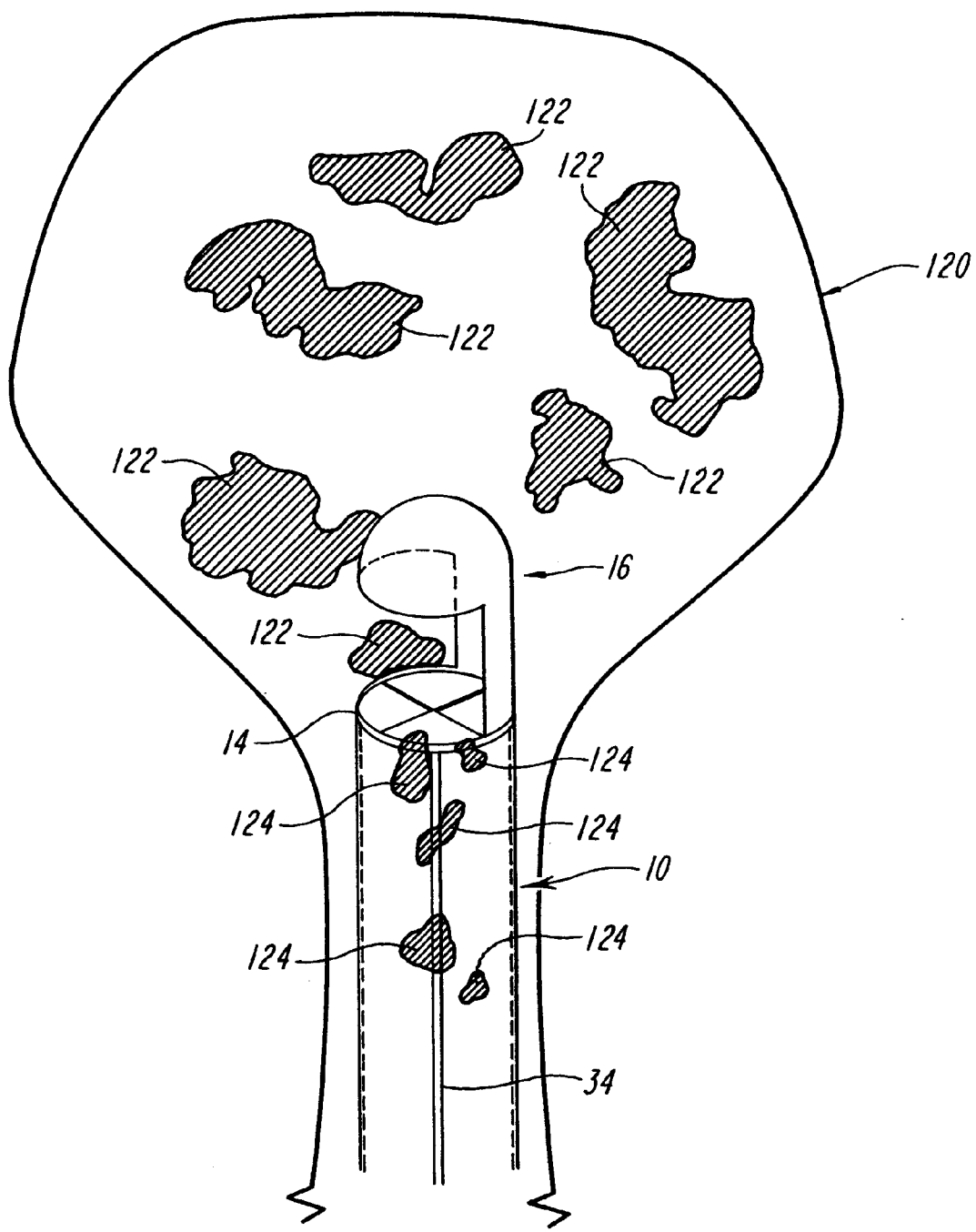
FIG. 5 is a schematic illustration of the operation of a clot evacuation catheter according to the present invention.

Referring now to FIG. 5, the clot evacuation catheter 10 of FIG. 1 is shown disposed in the bladder 120 or other body area. The catheter 10 may enter and be maneuvered through the bladder 120 as is generally known in the art in order to be able to evacuate any clots 122 present in the bladder. Although the catheter 10 shown in FIG. 7 is of the type depicted in FIG. 1, an embodiment of the type depicted in FIG. 4 may alternatively be used.

The catheter 10 may be placed into the bladder 120 or other body area to specifically cut clots 122 that are known to be present therein. Alternatively, the catheter 10 may be placed into the bladder 120 or other body area in anticipation of the appearance of clots 122. For example, the catheter 10 may be placed into the bladder 120 either before, during or immediately following bladder pathology or surgery. Cut clots 124 are forced proximal to the cutting blade 14 and through the tubular body 12 of the catheter 10 and are collected as is generally known in the art.

In an exemplary embodiment, the catheter 10 of FIGS. 1, 4, or 5 may have certain dimensions. For example, the tubular body 12 may have a longitudinal length between about 200 millimeters to 500 millimeters, and a diameter 32 between about 2.9 millimeters to 9.9 millimeters. Further, the outer lumen 22 may have a longitudinal length between about 200 millimeters to 500 millimeters, and a diameter 30 of between about 3.0 millimeters to 10.0 millimeters. The irrigation lumen 34 may have a diameter 38 and a longitudinal length that are, respectively, between about 0.5 millimeter to 2.0 millimeters and about 200 millimeters to 500 millimeters. The hood member 16, when included, may have a distal end 17 diameter between about 4.0 millimeters to 9.0 millimeters.

The present invention also contemplates embodiments of the catheters 10 of FIGS. 1, 4, or 5 in which a tubular body 12 is not disposed within an outer lumen 22. In such embodiments, the tubular body 12 would have a similar diameter 30 to the embodiments of FIGS. 1, 4 and 5, but also would also have a thicker outer wall that houses a port or channel. The port or channel would be adapted to provide air compression or liquid force to rotate the cutting blade 14 of the catheter 10. The catheter 10 would otherwise be substantially similar in its components, dimensions and operation to either of the catheters described with respect to FIGS. 1, 4, and 5.

Further, the catheter 10 of the present invention may optionally include a balloon or other device for maintaining the catheter in an indwelling position within a body cavity without requiring the use of a Foley catheter as shown in FIGS. 4 and 5.

Although the invention has been shown and described with respect to exemplary embodiments thereof, various other changes, omissions and additions in form and detail thereof may be made therein without departing from the spirit and scope of the invention. All references and publications cited herein are expressly incorporated herein by reference in their entirety.

What is claimed is:

1. A clot evacuation catheter, comprising:
   an outer lumen having a longitudinal axis and an open distal end;
   an elongate tubular body having a proximal end and a distal portion with an opening therein, the tubular body being disposed within the outer lumen and having a longitudinal axis coaxial with the longitudinal axis of the outer lumen and along which a vacuum force is selectively directed;
   a disk-shaped cutting blade having at least one opening disposed therein, the cutting blade being disposed within the distal portion of the tubular body and being selectively rotatable in a plane transverse to the longitudinal axis of the tubular body, wherein the cutting blade maintains a substantially fixed longitudinal locus during rotation; and
   a fluid conveying irrigation lumen disposed and extending longitudinally within the catheter, the irrigation lumen having an open distal end proximal to the cutting blade.

2. The catheter of claim 1, wherein the cutting blade is disposed proximal to a distal end of the tubular body by a distance between about 0.1 millimeter and 1.0 millimeter.

3. The catheter of claim 2, wherein the cutting blade has an outer rim portion and opposed wedge-shaped members, each separated by a wedge-shaped opening.

4. The catheter of claim 3, wherein each of the wedge-shaped members of the cutting blade has a substantially constant thickness of between about 0.1 millimeter to 2.0 millimeters.

5. The catheter of claim 1, wherein the tubular body is substantially cylindrical and has a substantially constant diameter of between about 3.0 millimeters and 10.0 millimeters.

6. The catheter of claim 1, wherein the cutting blade is mounted to an inner wall of the tubular body such that the tubular body and the cutting blade are selectively rotatable with each other.

7. The catheter of claim 1, wherein the cutting blade is made of a material selected from the group consisting of polymers, ceramics and metals.

8. The catheter of claim 7, wherein the cutting blade material is coated with polytetrafluoroethylene.

9. The catheter of claim 1, wherein the catheter has an opening at a distal end thereof that is coaxial with the longitudinal axis of the tubular body.

10. The catheter of claim 9, further comprising a hood member formed on the distal portion of the tubular body and extending distally from the opening at the distal end of the tubular body, the hood member having a distal end that is spaced from but coaxial with the opening of the catheter and an opening in a side portion thereof that is in communication with the opening of the distal end of the catheter.

11. A clot evacuation catheter, comprising:

an outer lumen having a longitudinal axis and an open distal end;

an elongate tubular body having a proximal end and a distal portion with an opening therein, the tubular body being disposed within the outer lumen and having a longitudinal axis coaxial with the longitudinal axis of the outer lumen and along which a vacuum force is selectively directed;

a cutting blade disposed within the distal portion of the tubular body and being selectively rotatable in a plane transverse to the longitudinal axis of the tubular body, the cutting blade being substantially disk-shaped with at least one opening disposed therein; and a fluid conveying irrigation lumen disposed and extending longitudinally within the catheter, the irrigation lumen having an open distal end proximal to the cutting blade;

a motive force provider in communication with the tubular body;

a vacuum source, in communication with the tubular body;

a vacuum force sensor in communication with the tubular body; and a control element in communication with the vacuum source, the vacuum force sensor and the motive force provider, effective to activate the vacuum source and the motive force provider when the vacuum force within the tubular body exceeds a predetermined value.

12. The catheter of claim 11, wherein the predetermined value of vacuum force is in excess of 40 cm $H_2O$.

13. The catheter of claim 11, wherein the cutting blade is disposed proximal to a distal end of the tubular body by a distance between about 0.1 millimeter and 1.0 millimeter.

14. The catheter of claim 13, wherein the cutting blade has an outer rim portion and opposed wedge-shaped members, each separated by a wedge-shaped opening.

15. The catheter of claim 14, wherein each of the wedge-shaped members of the cutting blade has a substantially constant thickness of between about 0.1 millimeter to 2.0 millimeters.

16. The catheter of claim 11, wherein the tubular body is substantially cylindrical and has a substantially constant diameter of between about 3.0 millimeters and 10.0 millimeters.

17. The catheter of claim 11, wherein the cutting blade is mounted to an inner wall of the tubular body such that the tubular body and the cutting blade are selectively rotatable with each other.

18. The catheter of claim 11, wherein the cutting blade is made of a material selected from the group consisting of polymers, ceramics and metals.

19. The catheter of claim 18, wherein the cutting blade material is coated with polytetrafluoroethylene.

20. The catheter of claim 11, wherein the catheter has an opening at a distal end thereof that is coaxial with the longitudinal axis of the tubular body.

21. The catheter of claim 20, further comprising a hood member formed on the distal portion of the tubular body and extending distally from the opening at the distal end of the tubular body, the hood member having a distal end that is spaced from but coaxial with the opening of the catheter and an opening in a side portion thereof that is in communication with the opening of the distal end of the catheter.

* * * * *